United States Patent
Eidman (10) Patent No.: US 10,849,998 B1
(45) Date of Patent: Dec. 1, 2020

(54) SANITIZATION DEVICE FOR FOOTWEAR

(71) Applicant: Brett Eidman, West Nyack, NY (US)

(72) Inventor: Brett Eidman, West Nyack, NY (US)

( * ) Notice: Subject to any disclaimer, the term of this patent is extended or adjusted under 35 U.S.C. 154(b) by 0 days.

(21) Appl. No.: 17/000,307

(22) Filed: Aug. 22, 2020

Related U.S. Application Data (63) Continuation of application No. 16/563,859, filed on Sep. 7, 2019, now Pat. No. 10,765,769.

(60) Provisional application No. 62/729,803, filed on Sep. 11, 2018.

(51) Int. Cl.
*A61L 2/10* (2006.01)
*H02J 7/00* (2006.01)

(52) U.S. Cl.
CPC .............. *A61L 2/10* (2013.01); *H02J 7/0042* (2013.01); *H02J 7/0047* (2013.01)

(58) Field of Classification Search
CPC .......... A61L 2/10; A61L 2202/14; A61L 2/24; A61L 2/26; A61L 2/0047; A61L 2/202; A47L 23/02; A47L 2601/10; A47L 23/266; B08B 7/0057; B08B 7/0035; G01N 21/33
USPC ............. 250/454.11, 431, 504 R; 422/22, 24
See application file for complete search history.

(56) References Cited

U.S. PATENT DOCUMENTS

| | | | |
|---|---|---|---|
| 4,765,039 A | 8/1988 | Rowlands et al. | |
| 5,792,712 A | 8/1998 | Hori et al. | |
| 6,233,776 B1 | 5/2001 | Blum et al. | |
| 6,258,435 B1 | 7/2001 | Staal | |
| 6,886,210 B2 | 5/2005 | Dean | |
| 8,241,565 B1 | 8/2012 | Abdul | |
| 8,631,533 B1 | 1/2014 | Gulian et al. | |
| 8,973,197 B2 | 3/2015 | Omidi | |
| 9,101,260 B2 | 8/2015 | Desu-Kalyanam | |
| 9,198,991 B2 | 12/2015 | Dombrowsky et al. | |
| 9,211,352 B2 | 12/2015 | Kassel et al. | |
| 9,272,058 B1 | 3/2016 | Montgomery | |
| 9,463,258 B2 | 10/2016 | Kassel et al. | |

(Continued)

FOREIGN PATENT DOCUMENTS

| | | |
|---|---|---|
| DE | 2451429 A1 | 5/1975 |
| DE | 2020100049601 U1 | 10/2010 |

(Continued)

OTHER PUBLICATIONS

Welle, Mary K., et al, Bacteria on The Soles of Patient-Issued Nonskid Slipper Socks, Orthopedic Nursing, Jan./Feb. 2019, vol. 38, #1 p. 33 et seq., National Association of Orthopedic Nurses.
Purisan, About Sole Sanitizer-Sole sanitizer, www.purisan.com/about, Jul. 4, 2019, pp. 1-2 and 1-2.
Cleveland, Jonnie, PathO3 FSD: Patented Pathogen Destroying Technology for Shoe Soles, Pathogen Solutions, Mar. 2018, pp. 1-13, 2016 HEPCO Medical, LLC dba GEMS.

(Continued)

*Primary Examiner* — David A Vanore
(74) *Attorney, Agent, or Firm* — Michael E. Zall (57) ABSTRACT

The present disclosure relates to a portable and foldable sanitization device for sanitization of a user's footwear. The device comprising a back panel housing and a front panel which are operatively coupled with each other through a coupling means. The back panel includes a dirt removal mat on which a user scrubs footwear to dislodge any solid particulate tagged with the footwear. Furthermore, the front panel includes a clear plastic UV transparent sheet and a UV transparent lattice type support structure along with ultra-violet (UV) radiation emitting sources. When the user places the footwear on the lattice type support structure, the presence of footwear is detected and UV radiation on the footwear, thereby sanitizing the footwear.

15 Claims, 8 Drawing Sheets

(56) References Cited

U.S. PATENT DOCUMENTS

| | | | |
|---|---|---|---|
| 9,579,410 | B2 | 2/2017 | Simmons et al. |
| 10,064,966 | B2 | 9/2018 | Kassel et al. |
| 10,765,769 | B2 * | 9/2020 | Eidman ................ H02J 7/0042 |
| 2010/0193709 | A1 | 8/2010 | Dalton |
| 2010/0296970 | A1 | 11/2010 | Trimarco et al. |
| 2012/0167325 | A1 | 7/2012 | Omidi |
| 2016/0175896 | A1 | 6/2016 | Montgomery |
| 2017/0000915 | A1 | 1/2017 | Cottone |

FOREIGN PATENT DOCUMENTS

| | | |
|---|---|---|
| FR | 2009581 | 7/1970 |
| FR | 2761255 A1 | 10/1998 |
| JP | 01313057 A | 12/1989 |
| JP | 3110425 U | 2/2016 |
| KR | 20090022921 A | 3/2009 |
| KR | 20140065028 A | 5/2014 |

OTHER PUBLICATIONS

Gonzalez, Murielle, CleanRoom Technology, www.cleanroomtechnology.com, Apr. 8, 2019, 2019,Path03Gen Solutions footwear sanitising stations put to work at Florida hospital, pp. 1-7.

McNamara, Damian, C. difficile travels on the soles of our shoes, Jul. 11, 2017, pp. 1-2. MDEdge Infectious Disease.

Koganti, Sreelatha, MD, et al, Evaluation of Hospital Floors as a Potential Source of Pathogen Dissemination Using a Nonpathogenic Virus as a Surrogate Marker, Infection control & hospital epidemiology Nov. 2016, vol. 37, No. 11 downloaded from http:/www.cambridge.org/core.

Dao, My Lien, Prevalence of Methicillin-Resistant *Staphylococcus aureus* (MRSA) and Clostridium difficile (C. dif.I) on Shoe soles, and Effect of their Exposure to the GEM's SoleMate Sanitizing Device (SSD), GEM's SoleMate Sanitizing Device, Date Unknown.

Saleh, Naveed, MD, You Can Get Sick From Germs on Hospital Floors, May 26, 2019, VeryWell Health, pp. 1-5.

* cited by examiner

SANITIZATION DEVICE FOR FOOTWEAR

RELATED APPLICATIONS

This application is a Continuation of non-provisional application Ser. No. 16/563,859 filed on Sep. 7, 2019, now U.S. patent Ser. No. 10/765,769, which claims priority of provisional applications 62/729,803 filed on Sep. 11, 2018. The entire disclosures of these provisional applications are incorporated herein by reference.

SPECIFICATION

Field of the Invention

The present invention generally relates to sanitization of footwear, and more particularly relates to a portable sanitization device incorporating a dirt removal mat and ultraviolet (UV) radiation emitting sources to disinfect the footwear of a user.

Background of the Invention

The Background of the Invention includes information that may be useful in understanding the present invention. It is not an admission that any of the information provided herein is prior art, relevant to the presently claimed invention, or that any publication specifically or implicitly referenced is prior art.

A floor mat is utilized by a user for wiping dirt off of his/her footwear or feet. The floor mat is primarily used to reduce solid particulates which are attached to the bottom of the footwear. After wiping on the mat, the footwear has reduced dirt and assists in minimizing and avoiding slips, trips, and falls and also keeps the location clean and hygienic.

Generally, the floor mat is widely accepted for cleaning the underneath of footwear and adopted even in various sensitive locations, for example, Intensive Care Units (ICU), surgery wings, sterile areas of a pharmaceutical manufacturing unit, food packaging and manufacturing locations etc. The user wearing the footwear walks on roads, public toilets, malls, parks, and other open areas from where the footwear is more prone to nosocomial infections/microorganisms. People having these infections embedded in the footwear when they visit these sensitive locations, contaminate the floor and at times become a primary source of spreading serious diseases to other people. These infections/microorganisms can be dangerous. Also, this can be particularly dangerous as people travel from country to country carrying microorganisms that are not indigenous to the region to which they are going.

In order to overcome spreading of these infections, various means to prevent transmission have been used. One wisely used method is to take off the footwear at the entrance to such areas and put on a sanitary shoe cover. However, taking off your shoes, and/or putting on sanitary shoe covers and then putting your shoes back on again can be a cumbersome process, particularly in residential areas, and the footwear can still transmit infections.

The following references may be relevant to the claimed invention:
U.S. Pat. No. 4,765,039 to Rowlands et al.; U.S. Pat. No. 5,792,712 to Hori et al; U.S. Pat. No. 6,233,776 to Blum et al; U.S. Pat. No. 6,258,435 to Staal; U.S. Pat. No. 6,886,210 to Dean; U.S. Pat. No. 8,241,565 to Abdul; U.S. Pat. No. 8,631,533 to Gullan et al; U.S. Pat. No. 8,973,197 to Omidi; U.S. Pat. No. 9,101,260 to Aishwarya; U.S. Pat. No. 9,198,991 to Dombrowski et al.; U.S. Pat. No. 9,272,058 to Montfomery; U.S. Pat. No. 9,579,410 to Simmons et al.; US Publication 2010/0296970 to Trimarco et al.; US Publication 2012/0167325 to Omidi; US Publication 2016/0175896 to Montgomery; US Publication 2017/0000915 to Cottone; JP 3110425 U; JP 01313057 A; KR 20140065028; KR 20090022921; FR 2009581 A7; FR 2761255 A1; DE 202010004960 U1 and DE 2451429 A1.

Although various devices and systems have been proposed to sanitize footwear, for example with floor mats and disinfectants, they fail to disclose a device that has all of the elements and benefits of the device described and claimed herein.

SUMMARY OF THE INVENTION

The present invention generally relates to sanitization of footwear, and more particularly relates to a portable sanitization device incorporating dirt removal mat and ultraviolet (UV) radiation emitting sources to disinfect the footwear/foot of a user.

One embodiment of the present invention provides a sanitization device for sanitization of a footwear that comprises:
a back panel housing having an inner surface, an outer surface and surrounding edges;
a front panel housing having an inner surface, an outer surface and surrounding edges;
a coupling means included along a portion of the surrounding edges of each housing panel arranged to foldably couple the back panel housing and the front panel housing to i) permit the folding of the housings toward each other to enable the inner surface of the front panel to face the inner surface of the back panel to form a closed sanitation device and ii) to permit the unfolding of the housings away from each other to enable the outer surface of the front panel and the outer surface of the back panel to be substantially coplanar to rest on a floor and form an open sanitation device;
the back panel housing comprises:
a dirt removal mat mounted to the inner surface of the back panel, wherein the dirt removal mat comprises one or more dirt removal means to remove the dirt from the footwear;
the front panel housing comprises a first compartment and a second compartment, wherein the second compartment is arranged on top of the first compartment;
the first compartment comprises:
a battery for direct current (DC) supply;
a ballast arranged to receive the direct current (DC) supply from the battery and convert the direct current (DC) supply into alternating current (AC) supply;
the second compartment comprises:
one or more ultraviolet (UV) radiation emitting sources, which when the UV radiation emitting sources receive the AC current supply, emit UV radiation;
one or more limit switches, wherein the one or more limit switches are arranged to control the AC current supply, to the one or more ultraviolet (UV) radiation emitting sources for a predetermined time interval;
a UV transparent layer overlaying the UV radiation emitting sources;
wherein when the opened sanitation device is positioned on the floor the user steps on the dirt removal mat to remove dirt from the footwear and then steps on the UV transparent layer to expose the footwear to the emitted UV radiation.

The one or more UV radiation emitting sources emit UV radiation with wavelength selected from a range of 10 nm to 400 nm.

In another embodiment, the UV transparent layer is made of a polymer material selected from the group of Cyclic Olefin Copolymer (COC), polypropylene, polyethylene, quartz, Poly (methyl methacrylate) (PMMA), Fluorinated Ethylene Propylene (FEP) and Polymethylpentene (PMP).

In yet another embodiment, the portable sanitization device further comprises a size detection means to detect the size and a surface area of the footwear.

In still another embodiment, the portable sanitization device further comprises a UV opaque layer wherein the UV opaque layer is arranged to cover a portion of the front panel housing to prevent the UV radiation emission escaping into the environment.

In yet another embodiment, the coupling means include one or more hinges.

In another embodiment, the portable sanitization device further comprises a charging unit to charge the battery.

In another embodiment, the portable sanitization device further comprises the charging cord stored below the dirt removal mat.

In another embodiment of the present invention the sanitization device further comprises: one or more sensors configured to sense the presence of the footwear;
  a UV transparent layer overlaying the UV radiation emitting sources;
  a memory unit;
  one or more processors, wherein the one or more processors are coupled to the memory unit and operable to execute the one or more routines, wherein the one or more routines include:
    a footwear presence sensor data retrieval engine, wherein the footwear presence sensor data retrieval engine retrieves a presence information of the footwear from the one or more sensors;
    a UV radiation emitting source activation engine, wherein the UV radiation emitting source activation engine is operable to activate the one or more UV radiation emitting sources to emit UV radiation, if presence of the footwear is determined; and
    a UV radiation emitting source control engine, wherein UV radiation emitting source control engine is operable to control the configured one or more UV radiation emitting sources, to emit the radiation of a predetermined wavelength for a predetermined period of time, on the footwear for sanitization.

The portable sanitization device may further include at least one indicator to indicate the footwear is sanitized.

In another embodiment the portable sanitization device further includes a sanitization status transmission engine, wherein the sanitization status transmission engine transmits the sanitization status of the footwear over a communication network to one or more electronic computing devices.

In an embodiment, the sensor is selected from a group of a temperature sensor, a proximity sensor, a pressure sensor, a motion sensor, a LIDAR sensor, a radio sensor, a hall effect sensor, a sound navigation ranging (Sonar) sensor, an occupancy sensor, a vibration sensor, an ultrasonic sensor, an image sensor, a piezoelectric sensor, a gyroscope, a passive infrared (PIR) sensor, a thermal sensor and a face recognition sensor.

The portable sanitization device may further include at least one indicator to indicate the battery status and/or a charging unit arranged to charge the battery.

Another aspect of this invention is directed to a method of sanitizing a user's footwear, the method comprising:
  providing the aforedescribed portable sanitization device;
  unfolding of the back panel housing and the front panel housing away from each other to enable an outer surface of the front panel and an outer surface of the back panel to be substantially coplanar to rest on a floor and form an open sanitation device;
  placing the open portable sanitization device on the floor;
  placing the footwear, on the dirt removal mat, arranged on an inner surface of a back panel housing;
  scrubbing, the footwear on the dirt removal mat, to remove the dirt from the footwear;
  placing the footwear on an inner surface of a front panel housing; and
  activating one or more ultraviolet (UV) radiation emitting sources to emit UV radiation of a predetermined wavelength for a predetermined period of time for the sanitization of the footwear; and
  removing the footwear from the front panel housing.

Various objects, features, aspects and advantages of the inventive subject matter will become more apparent from the following detailed description of preferred embodiments, along with the accompanying drawing figures in which like numerals represent like components

BRIEF DESCRIPTION OF THE DRAWINGS

Other features and advantages of the present invention will become apparent from the following more detailed description, taken in conjunction with the accompanying drawings, which illustrate, by way of example, the principles of the invention.

The drawings are not presented to scale but are only used to illustrate the principles of the invention. In the drawings, like reference numbers indicate like elements.

DETAILED DESCRIPTION OF THE INVENTION

The following is a detailed description of embodiments of the invention depicted in the accompanying drawings. The embodiments are in such detail as to clearly communicate the invention. However, the amount of detail offered is not intended to limit the anticipated variations of embodiments; on the contrary, the intention is to cover all modifications, equivalents, and alternatives falling within the spirit and scope of the present invention as defined by the appended claims.

Figure 1:
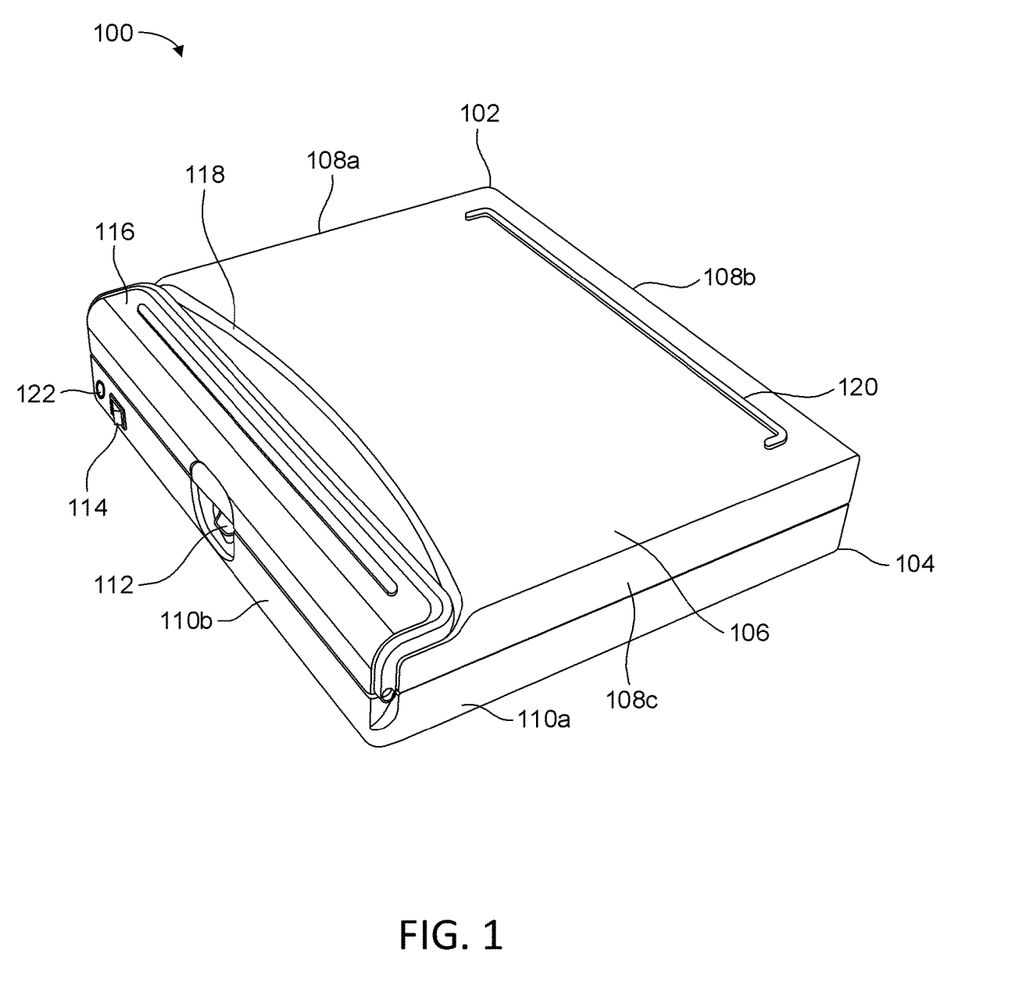
FIG. 1. is a perspective view of the folded portable sanitization device, in accordance with embodiments of the present disclosure.

FIG. 1, is a perspective view of the folded portable sanitization device 100. The portable sanitization device 100 includes two surfaces namely the back panel housing 102 and the front panel housing 104. The back panel housing 102 is affixed on top of the front panel housing 104.

The back panel housing 102 includes the outer surface 106, the inner surface (not shown) opposite to the outer surface 106, and the four surrounding edges 108a, 108b, 108c and an edge (not shown) opposite to the 108b. Collectively and interchangeably the four surrounding edges referred to as surrounding edges 108 hereinafter.

Still referring to FIG. 1, the front panel housing 104 includes the outer surface (not shown) that acts as a base on which the portable sanitization device 100 rests on the floor/ground, the inner surface (not shown) which is opposite to the outer surface of the front panel housing 104 and faces the inner surface of the back panel housing 102 during folded position, and four surrounding edges. The four surrounding edges are 110a, 110b, and two edges (not shown) opposite to 110a and 110b.

The back panel housing 102 and the front panel housing 104 are coupled with each other, through the coupling means (not shown). The coupling means are arranged along a portion of the surrounding edges 108 of the back panel housing 102 and/or the front panel housing 104 to permit folding and unfolding of the portable sanitization device 100. During folding of the portable sanitization device 100, the coupling means permits, the inner surface of back panel housing 102 and the inner surface of front panel housing 104 to face each other. In simple terms, the term "coupling means" as used herein refers to a mechanical arrangement, that when in operation, allows or restricts movement of the back panel housing 102 with respect to the front panel housing 104. As a non-limiting example of coupling means includes hinges, fabrics, a ball-and-socket joint, a swivel joint, a knuckle joint, revolute joint, bolted joint, screw joint, revolute joint, a helical joint, a joint, a rivet, a hook, and the like.

As seen in FIG. 1, when the sanitization device 100 is in folded position, the housings 102 and 104 are locked/engaged with each other through a lock/latch 112. The lock 112 is provided with two states, that is a locked state and an unlocked state. The lock 112 in the unlocked state allows the back panel housing 102 to move away from (unfold) the front panel housing 104 and restricts such when in the in the locked state (folded).

Still referring to FIG. 1, the portable sanitization device 100 may also include a power switch 114, an overlay 116, a handle 118, one or more legs 120 and a power inlet 122. The power inlet 122 enables a power chord to be inserted and charge an enclosed battery. In use, the power switch 114 is set to ON mode to enable power distribution among various electronics/electrical components of the portable sanitization device 100. However, when the power switch 114 is set in OFF mode, no power is supplied to such components. The overlay 116 is a flap kind of structure that extends from the surrounding edges of the front panel housing 104 and overlaps to the back panel housing 102. The overlay 116 can be made of rubber, leather, foam etc.

The sanitization device further includes a handle 118 that is used by the user to carry the portable sanitization device 100. The sanitization device 100 is light weight and portable and is easy for the user to relocate wherever the portable sanitization device 100 is required. The handle 118 can be used to unfold the folded portable sanitization device 100 and/or used to carry the folded sanitization device. The sanitization device 100 includes the one or more legs 120 to provide anti slip feature when the sanitization device is in unfolded position. It prevents the sanitization device from moving when a user is using the device for dirt removal and subsequent sanitization of footwear. The legs 120 assist in maintaining the unfolded sanitization device slightly above the ground. The legs 120 can be made of any material such as a rubber, a plastic, or combinations thereof or any other material that prevents slippage of the device 100 when placed on the ground. Although, only one leg 120 is depicted, a greater number of legs may be used. The front panel housing 104 can also comprise one or more legs 120.

Figure 2:
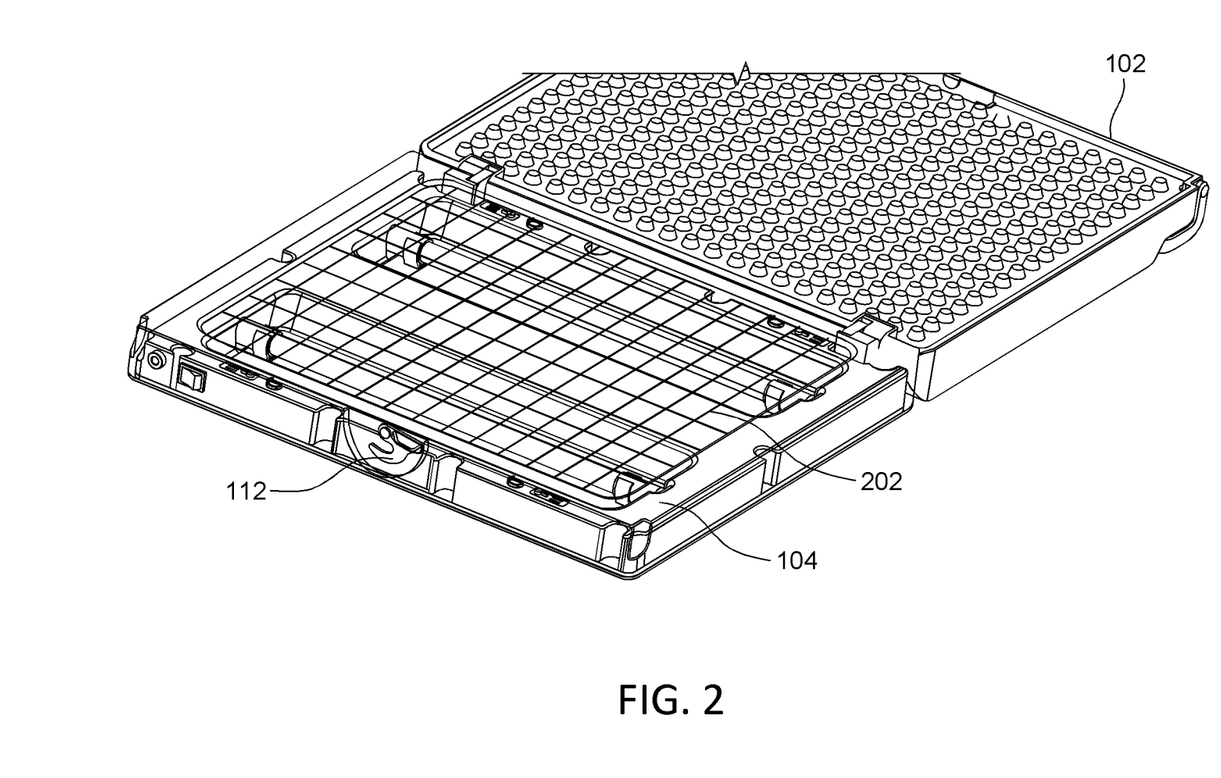
FIG. 2. is a perspective view of the unfolded portable sanitization device, in accordance with embodiments of the present disclosure.

FIG. 2. is a perspective view of the unfolded portable sanitization device 100. To unfold the portable sanitization device 100, the lock 112 is released to disengage the back panel housing 102 from the front panel housing 104. In one embodiment, the lock 112 can be released automatically when the user is in close proximity to the portable sanitization device 100. In another embodiment, the lock 112 can be released manually, through pressing a button, rotating a knob, and the like.

After the release of the lock 112, the back panel housing 102 and the front panel housing 104 are unfolded from each other and the back panel housing 102 and the outer surface of the front panel 104 are positioned to be substantially coplanar with each other to enable the device 100 to rest on the floor and form the unfolded portable sanitization device 100. A lattice type support panel 202 is affixed above the front panel 104 above a plastic UV transparent sheet (414) described below in reference to FIG. 4b. The lattice type support panel 202 may be made from, for example, Cyclic Olefin Copolymer (COC), polymeric material, polypropylene, polyethylene, quartz, Poly(methyl methacrylate) (PMMA), Fluorinated Ethylene Propylene (FEP) and Polymethylpentene (PMP) and may also be a metal lattice. The lattice 202 enables the UV radiation to pass through the lattice type support panel 202 to irradiate the footwear placed above it (described below).

Referring to FIG. 2, the portable sanitization device 100 may include one back panel housing 102 and one front panel housing 104. In another embodiment, the portable sanitization device 100 may include multiple back panel housings 102 and one front panel housing 104. In yet another embodiment, the portable sanitization device 100 may include multiple back panel housings 102 and multiple front panel housings 104. In alternate embodiment, the portable sanitization device 100 may include one back panel housing 102 and multiple front panel housings.

It is contemplated (not shown) that the coupling means attached to the panel housings 102 and 104 can enable connections between multiple portable sanitization devices. Additionally, it is contemplated that multiple housings 102 and 104 can enable multiple users to use multiple portable sanitization devices 100 simultaneously. In another embodiment, the back panel housing 102 and front panel housing 104 can be disconnected from each other and placed at some distance from each other, for an instance, 5-10 meters. Also, the back panel housing 102 can be placed right of the front panel housing 104 or to the left depending on different cultures, customs and/or interior configurations.

Although, the dimensions of the back panel housing 102 and the front panel housing 104 are shown to be about the same size and thickness, the length, width, thickness, design, material used for making both the panel housings 102 and 104 can be different.

Figure 3:
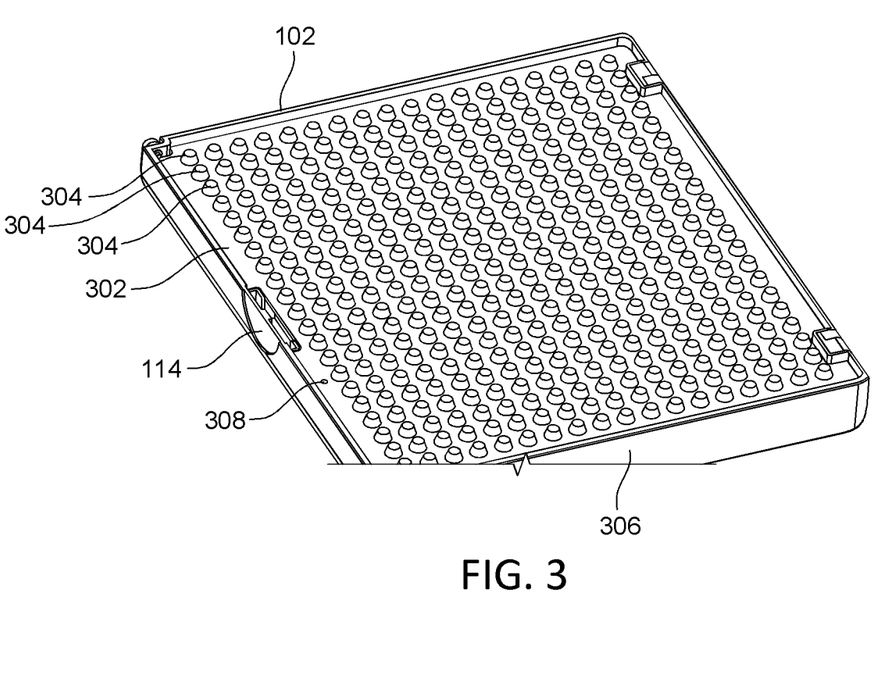
FIG. 3. is a perspective view showing the dirt removal mat in the unfolded portable sanitization device.

FIG. 3, a perspective view showing the various elements of the back panel housing 102 and their relationship to each other. Notably, the back panel housing 102 includes in the inner surface the dirt removal mat 302 mounted therein. The inner surface of the back panel housing 102 includes grooves/recessed area in which the dirt removal mat 302 may be positioned or fitted via screws, hooks, Velcro, loop fastener assembly, an adhesive or other coupling means.

The dirt removal mat 302 can include a dirt removal means 304 such as apertures, treads, grips, bristles, engraved cups, convex structures, ridges, crumples, projection creases, dents, lumps, teeth structure on which the user scrubs or wipes the footwear to remove the dirt from the footwear. Under the dirt removal mat, a reservoir 306 can be arranged to receive dirt that is dislodged after scrubbing the footwear. The dirt removal mat 302 and the reservoir 306 can be detachable from the back panel housing 102 as it would be comfortable to wash the dirt removal mat 302 and the reservoir 306 to dispose of the collected dirt and dust.

The dirt removal mat 302 may be made of materials such as molded plastic, natural rubber (NR), silicone rubber, foam, silicone, styrene butadiene, chloroprene, fluorocarbon, polyisoprene, cut polymeric sheet, ethylene-propylene, polyurethane, and other polymeric materials, such as nylon-6 in form of a porous structure and may also include a water/fluid absorption layer capable of cushioning the feet. The portable sanitization device 100, and in particular the dirt removal mat 302, may further comprise a suitable drying mechanism to evaporate water, moisture, vapor or any other liquid material which may be present on the footwear.

In the embodiment depicted in FIG. 3, a sanitization indicator 308 can be placed in the portable sanitization device 100 to indicate the sanitization status of the footwear. The sanitization indicator(s) may be selected from a group of LED lights, a sound buzzer, and a vibrator. For example, a green LED illumination indicator can indicate that sanitization is complete, whereas yellow LED illumination indicator can indicate that sanitization is only partially complete and red color LED illumination can indicate that sanitization is required. The dirt removal mat 302 weight, dimensions, color, treads, grips, bristles/apertures, geometric shape can vary.

Figure 4A:
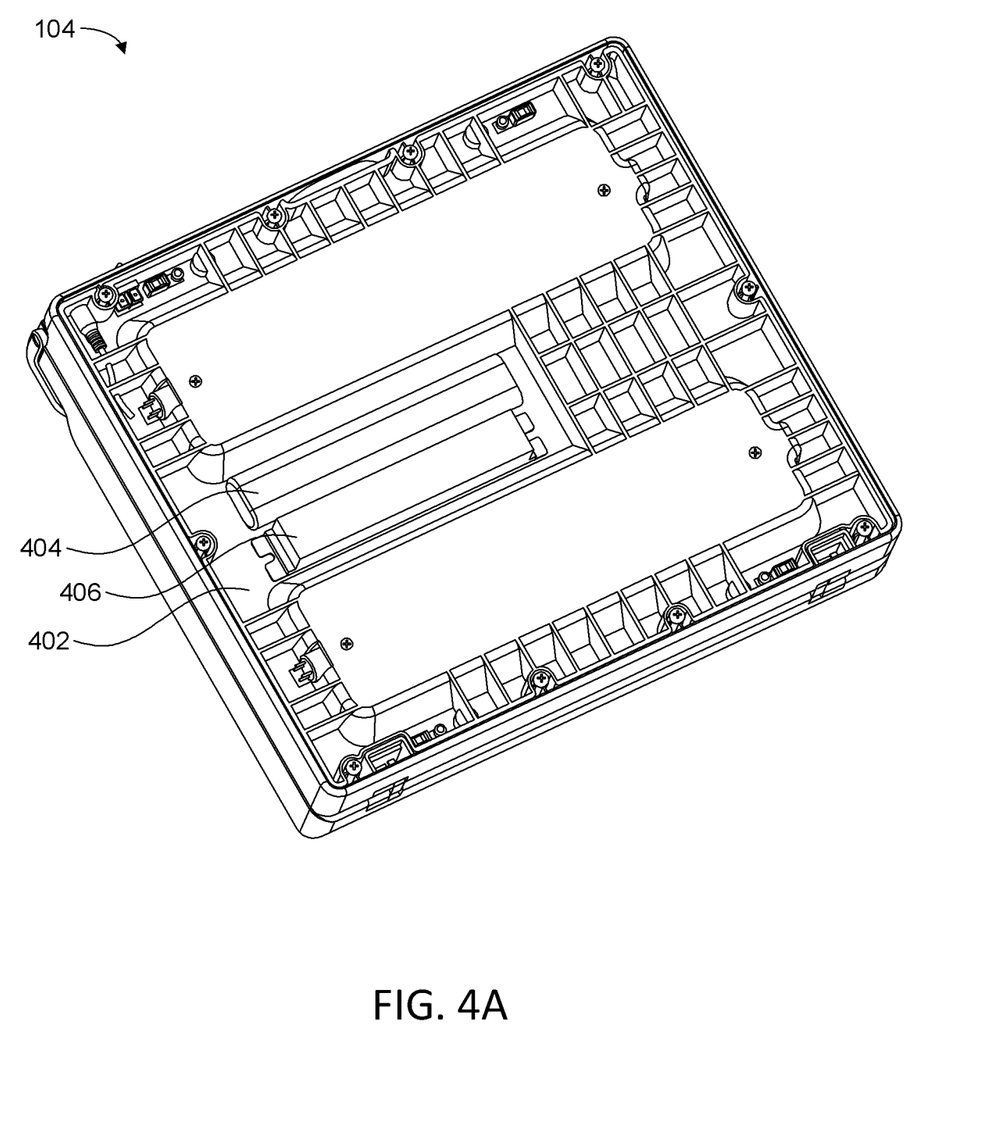
FIG. 4a is a perspective view showing the folded portable sanitization and the various elements of the front panel in the exposed first compartment including the housing and their relationship to each other.

FIG. 4A is a perspective view showing the various elements of the front panel 104 first compartment including the housing and their relationship to each other. Notably, after the user has scrubbed their footwear on the dirt removal mat 302, the user places the footwear on the front panel housing 104. The front panel housing 104 comprises two compartments, the first compartment 402 that comprises the battery 404 and the ballast 406.

Figure 4B:
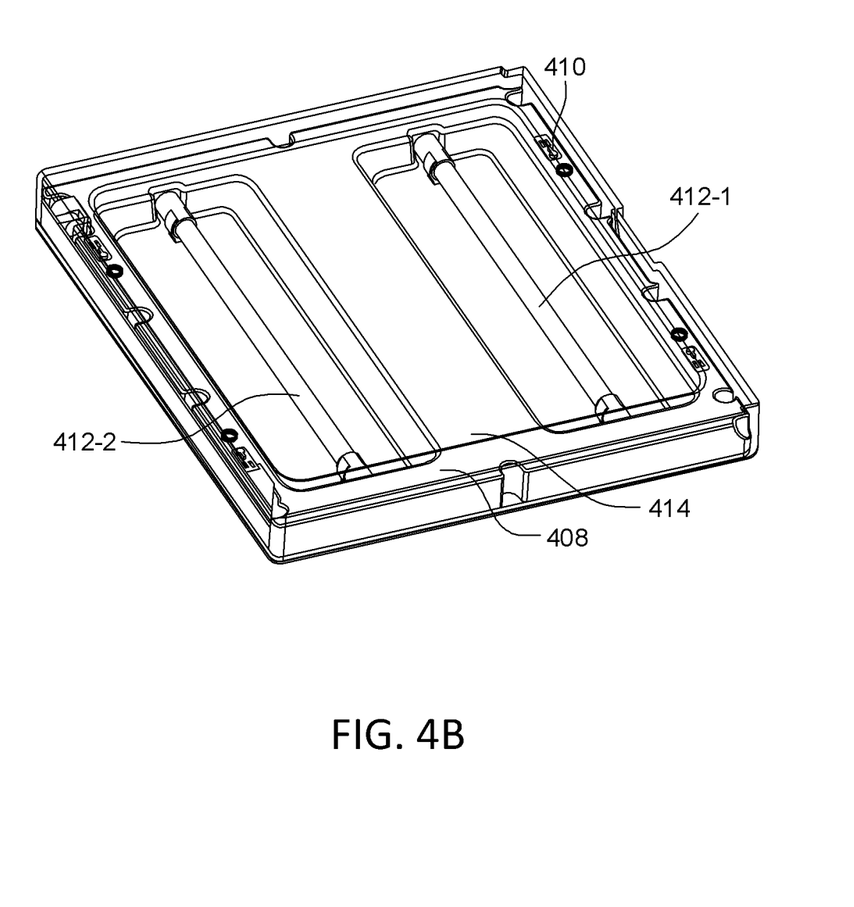
FIG. 4b is a perspective view showing the various elements of the front panel second compartment including the housing and their relationship to each other.

FIG. 4B is an perspective view showing the various elements of the front panel second compartment including the housing and their relationship to each other. The second compartment 408 is arranged on top of the first compartment 402 when viewing the sanitization device in unfolded position. The second compartment 408 comprises one or more limit switches/limit switch 410, the UV radiation emitting sources (412-1, 412-2 which are collectively and interchangeably referred to as UV radiation emitting sources 412 hereinafter) and the UV transparent layer 414 made of clear plastic that permits UV radiation therethrough.

Referring to FIGS. 4A and 4B, the battery 404, under the control of limit switches 410, supplies DC to the ballast 406. The ballast 406 is arranged to receive the DC from the battery 404 and convert received DC into AC. Although, the ballast 406 is configured for DC to AC conversion, however, any other electronic device, for an instance, a power inverter can be configured for DC to AC conversion. The ballast 406, after conversion of DC to AC, supplies AC to the ultraviolet (UV) radiation emitting sources 412.

The one or more limit switches 410 are arranged to control the supply of DC to the ballast 406. The term "control" refers that power is withdrawn by the battery 404 only whenever required by the portable sanitization device 100 and interrupt/stop thereafter. In one embodiment, DC is supplied only for a predetermined time interval after which DC supply can be interrupted. For an instance, DC is supplied to the ballast 406 only for 2 seconds, 15 seconds, 20 seconds, 60 seconds, 120 seconds, 150 seconds etc. or automatically when the user places the footwear on the portable sanitization device 100 or automatically when the user is in close proximity to the portable sanitization device 100. Beneficially, the limit switches 410 ensure avoidance of overflow of DC or supplying DC for a longer duration when the portable sanitization device 100 is not in use, thereby safeguards the components from damage. Once the ballast 406 receives DC supply, under the control of limit switches 410, the ballast 406 converts DC to AC and supplies AC to the ultraviolet (UV) radiation emitting sources 412.

The ultraviolet (UV) radiation emitting sources 412, responsive to receipt of the AC from the ballast 406, emits UV radiation with wavelength selected from a range of 10 nm to 400 nm. In simple terms, the wavelength can be 315 nm to 400 nm (ultraviolet A), 280 nm to 315 nm (ultraviolet B), 100 nm to 280 nm (ultraviolet C), 300 nm to 400 nm (near ultraviolet), 200 nm to 300 nm (middle ultraviolet), 122 nm to 200 nm (fair ultraviolet), 121 nm to 122 nm (Hydrogen Lyman-alpha), 10 nm to 200 nm (vacuum ultraviolet), 10 nm to 121 nm (extreme ultraviolet).

The UV transparent layer 414 overlays on the UV radiation emitting sources 412 to enable transfer of the emitted UV radiation to the footwear. The UV transparent layer 414 may be made from a polymeric material, for example, a Cyclic Olefin Copolymer (COC), polypropylene, polyethylene, quartz, Poly(methyl methacrylate) (PMMA), Fluorinated Ethylene Propylene (FEP) and Polymethylpentene (PMP).

When the UV transparent layer 414 receives the UV radiation from the UV radiation emitting sources 412, a UV opaque layer is also provided to prevent the UV radiation emission in areas other than the footwear area and only to the area that is occupied by the footwear.

Such footwear size and surface area can be detected by the footwear size detection means. In one embodiment, the UV opaque layer can be placed under the UV radiation emitting sources 412 to prevent the passing of UV radiation to the battery 404 and ballast 406. In such case, the emitted UV radiation can only be passed through the UV transparent layer 414 that is located above the UV radiation emitting sources 412. Additionally, a lattice type support panel 202 (FIG. 2) is also placed on top of the UV transparent layer 414. Both the UV transparent layer 414 and the lattice type support panel 202 in combination enable the sanitization device to support the weight of the user while stepping on the device to sanitize their footwear.

The battery 404, the ballast 406, the limit switches 410, the ultraviolet (UV) radiation emitting sources 412, and the UV transparent layer 414 may be fitted in separate sections.

Alternatively, all the battery 404, the ballast 406, the limit switches 410, the ultraviolet (UV) radiation emitting sources 412, and the UV transparent layer 414 can be encased in one, and supported by 416 the lattice type support panel.

In one embodiment, the limit switch 410 is lever arm that is located below the lattice type panel 416.

The components such as the battery 404, the ballast 406, the limit switches 410, the ultraviolet (UV) radiation emitting sources 412, and the UV transparent layer 414 are only exemplary and one or more other components can also be configured within the portable sanitization device 100. Such exemplary components can be a rectifier, an operational amplifier, a user weighing scale, a display screen etc. All such components are within the scope of the present disclosure.

In one embodiment, a charging unit can be arranged to charge the battery 404. The portable sanitization device 100 may further include at least one indicator (not shown) to indicate status of the battery 404. For example, the status of the battery 404 can be displayed on the display screen indicating the percent charged, a pointing device indicator can be utilized, different color LEDs to indicate different statuses such as full charge, low charging, medium level charging. The battery 404 can be charged through a power cord. The power cord can be arranged to be stored below or around the dirt removal mat 302. In an example, the charging can be performed through a wired means, a wireless means, an infrared source etc. The charging unit can be plugged into a standard 120 volt power outlet for the charging of the portable sanitization device 100.

The battery 404 can be a primary battery, a secondary (rechargeable) battery, Lithium-ion (Li-ion) battery, Nickel Cadmium (Ni—Cd) battery, Nickel-Metal Hydride (Ni-MH) battery, and Lead-Acid battery. Although the present disclosure describes only one battery 404, a greater number of batteries of the same or different types can be arranged in the portable sanitization device 100. In an example, a rechargeable lithium battery of 12 volts can be arranged to supply DC to the ballast 406.

Exemplary UV radiation emitting sources 412 can be UVC light emitting sources, bactericidal lamps, ultraviolet light tubes, a broad spectrum UV lamp, a clean room UV lamp, a compact UV lamp, a creative nail UV lamp, a deep UV lamp, a fluorescent UV lamp, a high intensity UV lamp, a high power UV lamp, a mercury UV lamp, a specialized UV gas-discharge lamp, a ultraviolet light-emitting diode (LED), a UV bulb, a UV electrodeless lamp, and an incandescent lamp. For exemplary purpose, the two germicidal bulbs of 17 Watt, 425 ma 42 Volt UV light tubes can be mounted to UV connectors which in turn are electrically connected to the ballast 406. In an embodiment, the UV radiating emitting sources 412 can be static and fixed in the electrical connectors to receive voltage and emit UV radiation. In another embodiment, the UV radiating emitting sources 412 can be fixed in the electrical connectors which in turn connected with a slider. When slider slides the UV radiating emitting sources 412 also slides.

Figure 5:
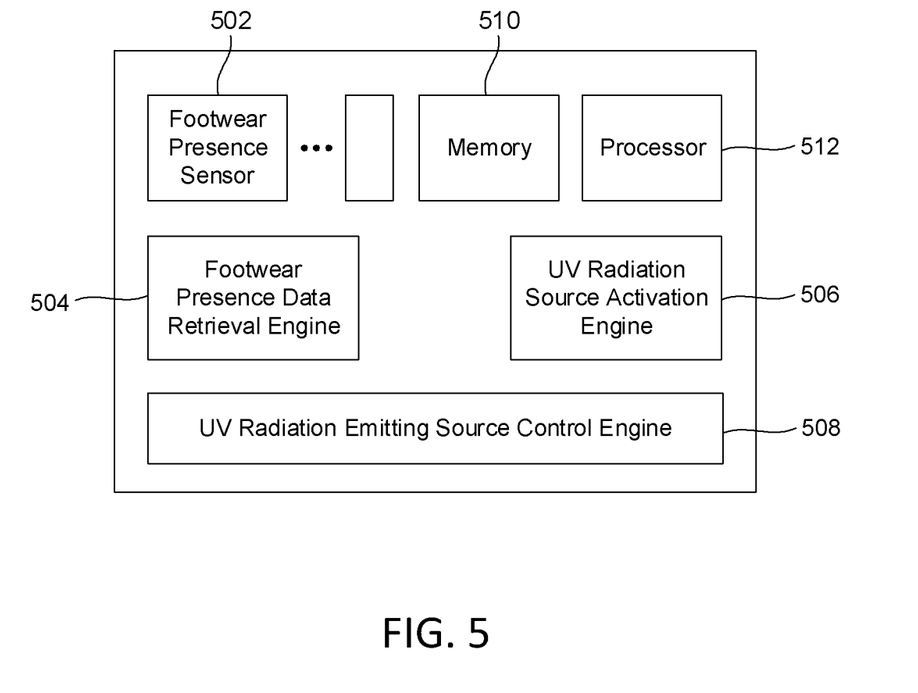
FIG. 5. is a representation of the sensors and different engines of the portable sanitization device and their relationship to each other.

FIG. 5, represents the sensors and different engines included in the portable sanitization device 100 and their relationship to each other. As mentioned above, the portable sanitization device 100 comprises the dirt removal mat 302, the battery 404, the ballast 406, the UV radiation emitting sources 412 and the UV transparent layer 414. The portable sanitization device 100 may also include the footwear presence detection sensor 502 and the engines such as the footwear presence sensor data retrieval engine 504, the UV radiation emitting source activation engine 506, and the UV radiation emitting source control engine 508. The footwear presence sensor data retrieval engine 504, the UV radiation emitting source activation engine 506 and the UV radiation emitting source control engine 508 are electronically and digitally communicably coupled with each other. The memory unit 510 and the processor 512 may also be included in the portable sanitization device 100. The memory unit 510 may have included therein routines associated with the engines which are operable by the processor 512.

In use, the user scrubs the footwear on the dirt removal mat 302 and then places the footwear on the front panel housing 104. The battery 404 supplies DC to the ballast 406 that converts DC to AC which is supplied to ultraviolet (UV) radiation emitting sources 412. Additionally, the ballast 406 also supplies AC to the memory unit 510, the processor 512 and the one or more sensors such as the footwear presence detection sensor 502. In an alternate embodiment, only the UV radiation emitting sources 412 operate on AC, other components such as sensors, memory unit 510 and processor 512 can operate on DC.

The footwear presence detection sensor 502, senses the presence of the footwear/user. The footwear presence detection sensor 502 may also communicate with other sensors, for example, an occupancy sensor to detect the user presence, a heartbeat sensor to sense heartbeat of the user to confirm human presence, an image sensor to recognize the user body parts shape, a passive infrared (PIR) sensor as PIR is sensitive to the user's skin, a proximity sensor to sense the user proximity with the portable sanitization device 100, an infrared detector, a temperature sensor, a pressure sensor, a motion sensor, a LIDAR sensor, a radio sensor, a hall effect sensor, a sound navigation ranging (sonar) sensor, a vibration sensor, an ultrasonic sensor, an image sensor, a piezoelectric sensor, a gyroscope, a face recognition sensor etc. The sensors may be configured for detecting the presence of a user. In response to the presence of a user, the sensor may send a signal to the portable sanitization device 100.

Such sensors may be included in, mounted to or in communication with the portable sanitizing device 100. For example, the sensors may be placed at a location that is away from the portable sanitizing device 100, but where the sensor can still detect the presence of a user. As a non-limiting example, the sensor may be placed at an entryway or above the portable sanitizing device 100. In some embodiments, the user may manually activate the portable sanitizing device 100 or by using a remote control or other method for sending a signal to the electrical circuit, which activates the portable sanitizing device 100.

Additionally, other footwear/foot related information can also be determined by the sensors such information include pressure, symmetry, timing, balance, orthotics, type of microorganism tagged, detailed images, statistical graphs pertaining to center of pressure and maximum pressure throughout plantar contact, size, surface area.

The footwear presence information determined by the footwear presence detection sensor 502, and/or other footwear/foot related information is transmitted to the footwear presence sensor data retrieval engine 504. The footwear presence sensor data retrieval engine 504, which when executed by the processor 512, processes footwear presence information and/or other footwear/foot related information. The processing of data confirms the footwear presence. The footwear presence sensor data retrieval engine 504 transmits the presence confirmation data to the operatively coupled UV radiation emitting source activation engine 506.

The UV radiation emitting source activation engine 506, which when executed by the processor 512, activate the one or more UV radiation emitting sources 412 to emit UV radiation. The UV radiation emitting source activation engine 506, activates the UV radiation emitting sources 412 for UV radiation emission, only if presence of the footwear is determined by the aforementioned sensors. If the footwear is not present over the front panel housing 104, no activation is performed. The UV radiation emitting source activation engine 506 communicates the activation information to the UV radiation emitting source control engine 508.

The UV radiation emitting source control engine 508, which when executed by the processor 512, upon receiving the activation information, controls the configured one or more UV radiation emitting sources 412, to emit the radiation of a predetermined wavelength for a predetermined period of time, on the footwear for sanitization. The emitted UV radiation is passed to the footwear through the UV transparent layer 414 to kill the microorganisms and complete sanitization.

The portable sanitization device 100 may additionally include a sanitization status transmission engine, wherein the sanitization status transmission engine transmits, over a communication network, the sanitization status of the footwear. The communication network may be a short-range communication and/or a long-range communication. The status is communicated to one or more electronic computing devices. In such case, the electronic computing devices can be selected from a group of a smartphone, a server, a laptop, a computer, and the like.

The portable sanitization device 100 may also include microorganism/microbes detection sensors to identify the category of microorganism that is tagged with the footwear. Exemplary microorganisms can be mycobacteria, *Clostridium difficile, Escherichia coli*, hepatitis A, B and C viruses, methicillin resistant *Staphylococcus aureus* (MRSA), *Mycobacterium tuberculosis, Nocardia asteroides, Pneumocystis carinii, Proteus mirabilis*, rotaviruses, rubella virus, *Staphylococcus aureus, Agalactiae, pyogenes*, tuberculosis, vancomycin-resistant *enterococcus, Viridans streptococcus* and any kind of pathogens that are capable of infecting.

The portable sanitization device 100 can be provided with USB port, card reader to transmit or receive various other software programs, say an advertisement to be displayed on the display screen configured on the portable sanitization device 100.

The portable sanitization device 100 may also be provided with heat dissipating mechanisms such as openings, fans which can continuously dissipate the heat generated due to operation of various electronic components.

The portable sanitization device 100 may also include a container to hold a liquid solution comprising a one or more disinfectants, multiple spraying jets to spray the liquid solution on various areas of the footwear. The spraying jets may be in communication with the processor 512 and various sensors. The processor 512 can selectively activate one or more jets to spray the liquid solution. The liquid solution comprising an alcohol (e.g. isopropyl alcohol, Ethyl alcohol), a peroxide (e.g. hydrogen peroxide), a chlorine backed (e.g. sodium hypochlorite), an aldehyde (e.g. formaldehyde, glutaraldehyde), an Iodophoric compound (e.g. Iodine solution), a phenolic compound (e.g. chloroxylenol, para-tertiary butylphenol, para-tertiary amylphenol), a quaternary ammonium compound (e.g. didecyl dimethyl ammonium bromide, fragrance/perfume, a deodorizing agent (e.g. a charcoal, an activated carbon, a zeolite, a silica gel, a bentonite, a carbon nanotube, an alumina etc.) and dioctyl dimethyl ammonium bromide) etc.

The portable sanitization device 100 can be utilized in various places such as a food processing facility, a hospital, a pharmaceutical production facility, a hotel, a house, a kitchen, a public toilet, an airport, a super market, a pathological/scientific laboratory, a research center, an university, a shopping mall/complex, a governmental establishments, an office, an old age home, a school, a college, an automobile, a kindergarten or any other suitable places where higher hygienic/aseptic environment is required.

The portable sanitization device 100 can be designed to accommodate different type footwear, e.g., boots, shoes, sneakers, heeled footwear, slippers, skates, sandals, flip flops, clogs, swimfins, sanitizing slippers, etc. depending on the environment in which it is used.

The portable sanitization device 100 can be coated with insulation layer. Such coating can be of ceramic, plastic, asbestos, glass, wooden, and the like.

The portable sanitization device 100 can be provided with rubber feet or an anti-slip elements 120 arranged on the bottom surface of the portable sanitization device 100 to keep the portable sanitizing device 100 in one place without movement during use.

Optionally, an antistatic agent can be deployed over the dirt removal means 304 to prevent dust particles from being aired when the user steps onto the back panel housing 102 or the front panel housing 104. The antistatic material may be any or a combination of long-chain aliphatic amines (optionally ethoxylated) and amides, quaternary ammonium salts (e.g., behentrimonium chloride or cocamidopropyl betaine), esters of phosphoric acid, polyethylene glycol esters, or polyols, and the like.

In operation, in order to enhance overall efficiency of the portable sanitization device 100, when emitted UV radiation is below 240 nm, $O_2$ molecules are split into two O atoms. The split $O_1$ atom combines with other $O_2$ molecules to form ozone. Ozone is very effective in killing microorganisms. Alternatively, the DNA of the microorganisms can be disrupted by the emitted UV radiation and sanitizes the footwear.

Figure 6:
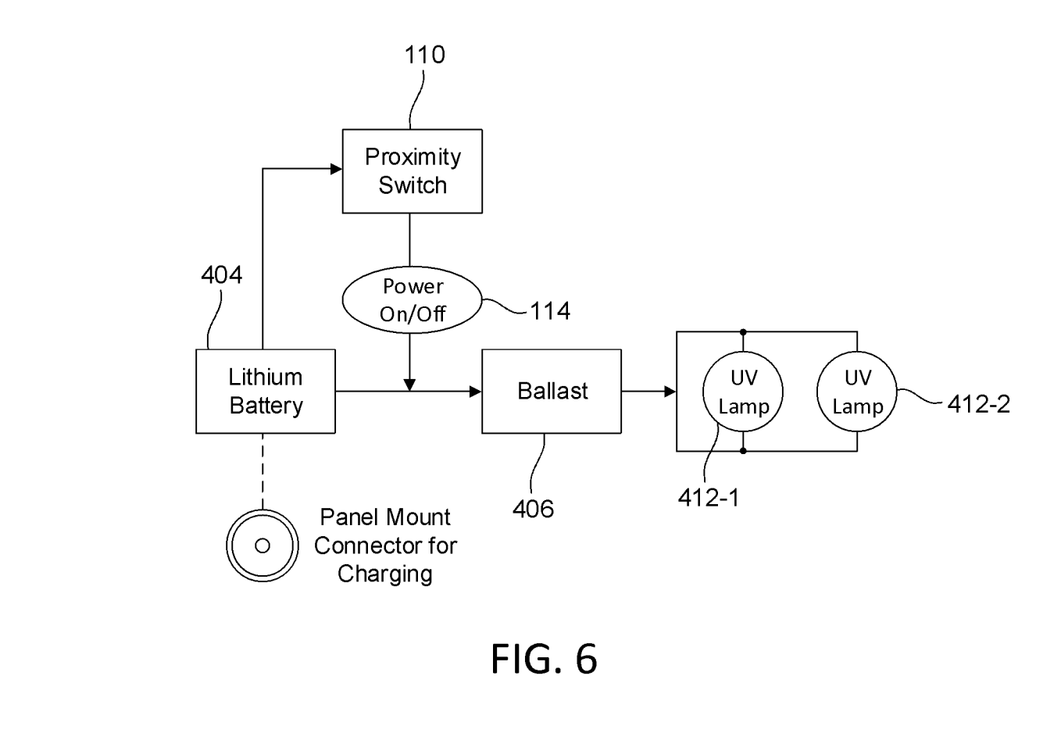
FIG. 6 is a schematic view illustrating the relationship between the various electrically connected elements of the portable sanitization device of this invention.

FIG. 6 is a schematic view illustrating the relationship between the various electrically connected elements of the portable sanitization device 100, in accordance with embodiments of the present disclosure. As illustrated, the battery 404, the ballast 406, the limit switches 410, the power switch 114 and the UV lamps 412-1 and 412-2 as ultraviolet (UV) radiation emitting sources are electrically connected with each other. Upon activating the ON mode of the power switch 114, the battery 404 supplies DC to the ballast 406 through the limit switches 410 to control the overflow of DC. The ballast 406 converts DC to AC and supplies AC to the two UV lamps 412-1 and 412-2. The UV lamps 412-1 and 412-2, upon receiving AC, emit UV radiation.

Figure 7:
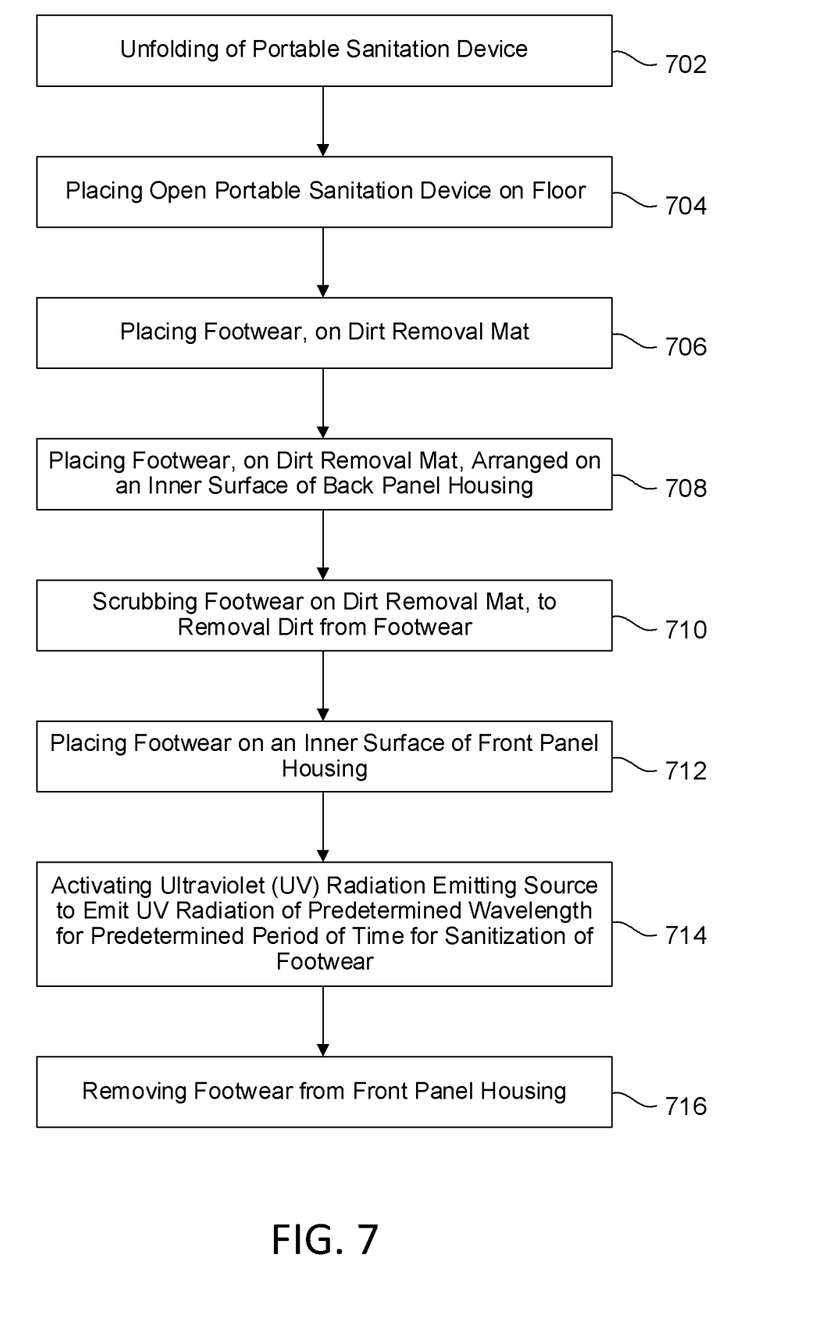
FIG. 7 illustrates an exemplary flow diagram depicting steps involved in the footwear sanitization process of this invention.

FIG. 7 illustrates an exemplary flow diagram depicting steps involved in footwear sanitization, in accordance with an embodiment of the present disclosure. In an implementation, the proposed method can include, a step (702), unfolding of the portable sanitation device 100; at step (706), placing the open portable sanitization device 100 on the floor, at step (708), placing the footwear, on the dirt removal mat 302, arranged on an inner surface of a back panel housing 102; at step (710), scrubbing, the footwear on the dirt removal mat 302, to remove the dirt from the footwear at step (712), placing the footwear on an inner surface of the front panel housing 104; and at step (714), activating one or more ultraviolet (UV) radiation emitting sources 412 to emit UV radiation of a predetermined wavelength for a predetermined period of time for the sanitization of the footwear; and at step (716), removing the footwear from the front panel housing 104. Further, the method also comprises: emitting the UV radiation of predetermined wavelength selected from range of 10 nm to 400 nm; detecting the size and the surface area of the footwear; notifying a sanitization status to the user; and folding the back panel housing 102 and the front panel housing 104 toward each other to enable the inner surface of the front panel 104 to face the inner surface of the back panel housing 102 to form a closed sanitation device 100.

| ELEMENTS | |
|---|---|
| Portable sanitization device | 100 |
| Back panel housing | 102 |
| Front panel housing | 104 |
| Outer surface | 106 |
| Surrounding edges of back panel housing | 108a, 108b, 108c |
| Surrounding edges of front panel housing | 110a and 110b |
| Lock/Latch | 112 |
| Power switch | 114 |
| Overlay | 116 |
| Handle | 118 |
| Leg | 120 |
| Power Inlet | 122 |
| Lattice type support panel | 202 |
| Dirt removal mat | 302 |
| Dirt removal means | 304 |
| Reservoir | 306 |
| Sanitization Indicator | 308 |
| First compartment | 402 |
| Battery | 404 |
| Ballast | 406 |
| Second compartment | 408 |
| Limit switches | 410 |
| UV radiation emitting sources | 412 |
| UV transparent layer | 414 |
| Footwear presence detection sensor | 502 |
| Footwear presence sensor data retrieval engine | 504 |
| UV radiation emitting source activation engine | 506 |
| UV radiation emitting source control engine | 508 |
| Memory unit | 510 |
| Processor | 512 |

The invention has been described with reference to various specific and illustrative aspects of the present invention and techniques. However, it should be understood that many variations and modifications may be made while remaining within the spirit and scope of the invention. Many alternatives, modifications and variations will be apparent to those skilled in the art in light of the foregoing description. Accordingly, this invention is intended to embrace all such alternatives, modifications, and variations that fall within the spirit and scope of the description.

The invention claimed is:

1. A portable sanitization device for sanitization of a user's footwear, the device comprising:
   a back panel housing having an inner surface, an outer surface and surrounding edges;
   a front panel housing having an inner surface, an outer surface and surrounding edges;
   a coupling means included along a portion of the surrounding edges of each housing panel arranged to foldably couple the back panel housing and the front panel housing to i) permit the folding of the housings toward each other to enable the inner surface of the front panel to face the inner surface of the back panel to form a closed sanitation device and ii) to permit the unfolding of the housings away from each other to enable the outer surface of the front panel and the outer surface of the back panel to be substantially coplanar to rest on a floor and form an open sanitation device;
   the back panel housing comprises:
      a dirt removal mat mounted to the inner surface of the back panel, wherein the dirt removal mat comprises one or more dirt removal means to remove the dirt from the footwear;
   the front panel housing comprises a first compartment and a second compartment, wherein the second compartment is arranged on top of the first compartment;
   the first compartment comprises:
      a source of alternating current (AC) supply;
   the second compartment comprises:
      one or more ultraviolet (UV) radiation emitting sources, which when the UV radiation emitting sources receive the AC current supply, emit UV radiation;
      one or more switches to control the AC current supply, to the one or more ultraviolet (UV) radiation emitting sources for a predetermined time interval;
      a UV transparent layer overlaying the UV radiation emitting sources;
      wherein when the opened sanitation device is positioned on the floor the user steps on the dirt removal mat to remove dirt from the footwear and then steps on the UV transparent layer to expose the footwear to the emitted UV radiation.

2. The portable sanitization device of claim 1, wherein the one or more UV radiation emitting sources emit UV radiation with wavelength selected from a range of 10 nm to 400 nm.

3. The portable sanitization device of claim 1, wherein the UV transparent layer is made of a polymer material selected from the group of Cyclic Olefin Copolymer (COC), polypropylene, polyethylene, quartz, Poly (methyl methacrylate) (PMMA), Fluorinated Ethylene Propylene (FEP) and Polymethylpentene (PMP).

4. The portable sanitization device of claim 1, further comprising a size detection means to detect the size and a surface area of the footwear.

5. The portable sanitization device of claim 1, further comprising a UV opaque layer wherein the UV opaque layer is arranged to cover a portion of the front panel housing to prevent the UV radiation emission into the environment.

6. The portable sanitization device of claim 1, wherein the coupling means include one or more hinges.

7. A method that provides sanitization of a user's footwear, the method comprising:
   providing the portable sanitization device of claim 1;
   unfolding of the back panel housing and the front panel housing away from each other to enable an outer surface of the front panel and an outer surface of the back panel to be substantially coplanar to rest on a floor and form an open sanitation device;
   placing the open portable sanitization device on the floor;
   placing the footwear, on the dirt removal mat, arranged on an inner surface of a back panel housing;
   scrubbing, the footwear on the dirt removal mat, to remove the dirt from the footwear,
   placing the footwear on an inner surface of a front panel housing; and
   activating one or more ultraviolet (UV) radiation emitting sources to emit UV radiation of a predetermined wavelength for a predetermined period of time for the sanitization of the footwear; and
   removing the footwear from the front panel housing.

8. The method of claim 7, wherein emitting the UV radiation of predetermined wavelength selected from a range of 10 nm to 400 nm.

9. The method of claim 7, further comprising a step of detecting a size and a surface area of the footwear.

10. The method of claim 7, further comprising a step of notifying a sanitization status to a user.

11. The method of claim 7, further comprising a step of folding the back panel housing and the front panel housing toward each other to enable the inner surface of the front panel to face the inner surface of the back panel to form a closed sanitation device.

12. A portable sanitization device for sanitization of a user's footwear, the device comprising:
- a back panel housing having an inner surface, an outer surface and surrounding edges;
- a front panel housing having an inner surface, an outer surface and surrounding edges;
- a coupling means included along a portion of the surrounding edges of each housing panel arranged to foldably couple the back panel housing and the front panel housing to i) permit the folding of the housings toward each other to enable the inner surface of the front panel to face the inner surface of the back panel to form a closed sanitation device and ii) to permit the unfolding of the housings away from each other to enable the outer surface of the front panel and the outer surface of the back panel to be substantially coplanar to rest on a floor and form an open sanitation device;
- the back panel housing comprises:
  - a dirt removal mat mounted to the inner surface of the back panel, wherein the dirt removal mat comprises one or more dirt removal means to remove the dirt from the footwear;
- the front panel housing comprises a first compartment and a second compartment, wherein the second compartment is arranged on top of the first compartment;
  - the first compartment comprises:
    - a source of alternating current (AC) supply;
  - the second compartment comprises:
    - one or more ultraviolet (UV) radiation emitting sources, which when the UV radiation emitting sources receive the AC current supply, emit UV radiation;
- one or more sensors configured to sense presence of the footwear;
- a UV transparent layer overlaying the UV radiation emitting sources;
- a memory unit;
- one or more processors, wherein the one or more processors are coupled to the memory unit and operable to execute the one or more routines, wherein the one or more routines include:
  - a footwear presence sensor data retrieval engine, wherein the footwear presence sensor data retrieval engine retrieves a presence information of the footwear from the one or more sensors;
  - a UV radiation emitting source activation engine, wherein the UV radiation emitting source activation engine is operable to activate the one or more UV radiation emitting sources to emit UV radiation, if presence of the footwear is determined; and
  - a UV radiation emitting source control engine, wherein UV radiation emitting source control engine is operable to control the configured one or more UV radiation emitting sources, to emit the radiation of a predetermined wavelength for a predetermined period of time, on the footwear for sanitization.

13. The portable sanitization device of claim 12, further comprising at least one indicator to indicate the footwear is sanitized.

14. The portable sanitization device of claim 12, further comprising a sanitization status transmission engine, wherein the sanitization status transmission engine transmits the sanitization status of the footwear over a communication network to one or more electronic computing devices.

15. The portable sanitization device of claim 12, wherein the sensor is selected from a group of a temperature sensor, a proximity sensor, a pressure sensor, a motion sensor, a LIDAR sensor, a radio sensor, a hall effect sensor, a sound navigation ranging (Sonar) sensor, an occupancy sensor, a vibration sensor, an ultrasonic sensor, an image sensor, a piezoelectric sensor, a gyroscope, a passive infrared (PIR) sensor, a thermal sensor and a face recognition sensor.

\* \* \* \* \*